(12) United States Patent
Jain et al.

(10) Patent No.: US 9,107,565 B2
(45) Date of Patent: Aug. 18, 2015

(54) IDENTIFYING AN EVENT OCCURRENCE FROM SENSOR DATA STREAMS

(75) Inventors: Jawahar Jain, Santa Clara, CA (US); David L. Marvit, San Francisco, CA (US)

(73) Assignee: Fujitsu Limited, Kawasaki (JP)

(*) Notice: Subject to any disclaimer, the term of this patent is extended or adjusted under 35 U.S.C. 154(b) by 298 days.

(21) Appl. No.: 12/856,799

(22) Filed: Aug. 16, 2010

(65) Prior Publication Data

US 2012/0042326 A1 Feb. 16, 2012

(51) Int. Cl.
*A61B 5/00* (2006.01)
*G01D 21/00* (2006.01)
*G06Q 10/10* (2012.01)
*G08C 15/00* (2006.01)

(52) U.S. Cl.
CPC .............. *A61B 5/00* (2013.01); *A61B 5/0022* (2013.01); *G01D 21/00* (2013.01); *G06Q 10/10* (2013.01); *G08C 15/00* (2013.01)

(58) Field of Classification Search
CPC .............. G06F 9/542; G06F 17/30516; G06F 17/30811; G06F 19/3406; G06F 3/0488; G06F 3/041; G06F 21/50; G06F 2203/0381; G06F 2203/04808; G06F 3/011; G06F 3/016; G06F 3/017; G06F 3/0237; G06F 3/03544; G06F 3/0383; G01N 27/3274; G01N 2021/1793
See application file for complete search history.

(56) References Cited

U.S. PATENT DOCUMENTS

| | | | | |
|---|---|---|---|---|
| 5,214,409 | A | 5/1993 | Beigel | 340/572.1 |
| 5,257,011 | A | 10/1993 | Beigel | 340/572.1 |
| 5,801,618 | A | 9/1998 | Jenkins | 340/426.14 |
| 6,960,986 | B2 | 11/2005 | Asama et al. | 340/10.41 |
| 6,988,667 | B2 | 1/2006 | Stewart et al. | 235/492 |
| 6,998,985 | B2 | 2/2006 | Reisman et al. | 340/573.1 |
| 7,262,686 | B2 | 8/2007 | Stewart et al. | 340/10.41 |
| 7,598,857 | B1 | 10/2009 | Reagan et al. | 340/539.22 |
| 7,626,545 | B2 | 12/2009 | Smith et al. | 342/451 |

(Continued)

FOREIGN PATENT DOCUMENTS

| | | | |
|---|---|---|---|
| JP | H10-113343 | 5/1998 | |
| JP | 2004102859 | 4/2004 | G06K 17/00 |

(Continued)

OTHER PUBLICATIONS

U.S. Appl. No. 12/856,780 entitled "Selecting Metadata for Sensor Data Streams", by B. Thomas Adler, et al, 30 pages of specification, claims, abstract, and drawings, filed Aug. 16, 2010.
British Search Report under Section 17(5); Appilcation No. GB-1113328.7; pp. 6, Dec. 2, 2011.
British Search Report; Application No. GB1113850.0; pp. 4, Nov. 7, 2011.

(Continued)

*Primary Examiner* — Tuan Dao
(74) *Attorney, Agent, or Firm* — Baker Botts L.L.P.

(57) ABSTRACT

According to one embodiment of the present invention, a method for identifying the occurrence of an event from sensor data streams may be provided. The method may include accessing a plurality of sensor data streams generated by a plurality of sensor sets. Each sensor set may comprise one or more sensors. A sensor data stream may be associated with a user. The user may be co-located with a sensor set that generates the sensor data stream. A relationship between two or more sensor data streams of the plurality of sensor data streams may be identified. The method may further include determining, according to the relationship, that the plurality of sensor data streams corresponds to an event. A notification of an occurrence of the event may be sent.

18 Claims, 2 Drawing Sheets

(56) References Cited

U.S. PATENT DOCUMENTS

| | | | |
|---|---|---|---|
| 7,634,115 B2 | 12/2009 | Ryu | 382/118 |
| 7,756,322 B2 | 7/2010 | Saitou et al. | 382/153 |
| 7,822,508 B2 | 10/2010 | Sugiyama et al. | 700/245 |
| 7,822,710 B1 | 10/2010 | Miller et al. | 707/620 |
| 7,852,217 B2 | 12/2010 | Kondo et al. | 340/572.1 |
| 8,010,231 B2 | 8/2011 | Sumida et al. | 700/253 |
| 8,094,012 B1 | 1/2012 | Tran et al. | 340/539.13 |
| 2001/0052842 A1 | 12/2001 | Asama et al. | 340/10.41 |
| 2004/0174264 A1 | 9/2004 | Reisman et al. | 340/573.4 |
| 2005/0211787 A1 | 9/2005 | Stewart et al. | 235/492 |
| 2006/0106581 A1 | 5/2006 | Bornhoevd et al. | 702/188 |
| 2007/0063850 A1* | 3/2007 | Devaul et al. | 340/573.1 |
| 2007/0176779 A1 | 8/2007 | Braunstein | 340/572.1 |
| 2007/0200701 A1 | 8/2007 | English et al. | 340/572.1 |
| 2007/0262851 A1 | 11/2007 | Stewart et al. | 340/10.41 |
| 2008/0055158 A1 | 3/2008 | Smith et al. | 342/464 |
| 2008/0061962 A1 | 3/2008 | Campman | 340/539.13 |
| 2008/0204218 A1 | 8/2008 | Tupman et al. | 340/501 |
| 2008/0252426 A1 | 10/2008 | Lee et al. | 340/10.3 |
| 2008/0301175 A1* | 12/2008 | Applebaum et al. | 707/102 |
| 2009/0002133 A1 | 1/2009 | Braunstein | 340/10.42 |
| 2009/0119843 A1* | 5/2009 | Rodgers et al. | 5/611 |
| 2009/0148034 A1 | 6/2009 | Higaki et al. | 382/153 |
| 2009/0149991 A1 | 6/2009 | Sumida et al. | 700/246 |
| 2009/0233633 A1 | 9/2009 | Morrison | 455/466 |
| 2009/0234810 A1* | 9/2009 | Angell et al. | 707/3 |
| 2009/0256678 A1 | 10/2009 | Ryu | 340/5.83 |
| 2009/0273468 A1 | 11/2009 | Mazar et al. | 340/539.12 |
| 2010/0052891 A1 | 3/2010 | Chainer et al. | 340/517 |
| 2010/0073235 A1 | 3/2010 | Smith et al. | 342/451 |
| 2010/0106853 A1* | 4/2010 | Kashiyama et al. | 709/231 |
| 2010/0109844 A1 | 5/2010 | Carrick et al. | 340/10.1 |
| 2010/0109903 A1 | 5/2010 | Carrick | 340/825.49 |
| 2010/0127824 A1 | 5/2010 | Moschl et al. | 340/5.65 |
| 2010/0250021 A1* | 9/2010 | Cook et al. | 701/1 |
| 2010/0287161 A1* | 11/2010 | Naqvi | 707/740 |
| 2011/0125000 A1 | 5/2011 | Rantala | 600/372 |
| 2012/0216041 A1 | 8/2012 | Naono et al. | 713/171 |

FOREIGN PATENT DOCUMENTS

| | | | | |
|---|---|---|---|---|
| JP | 2005018221 | 1/2005 | | B60K 26/02 |
| JP | 2005084440 | 3/2005 | | G03B 27/62 |
| JP | 2009058999 | 3/2009 | | G08B 25/04 |
| JP | 2010-517565 | 5/2010 | | |
| WO | WO 95/05627 | 2/1995 | | G05B 19/00 |
| WO | WO 2007074671 | 7/2007 | | G01S 13/78 |
| WO | WO 2010/068582 | 6/2010 | | G01R 21/133 |
| WO | WO 2011/067675 | 6/2011 | | G06Q 30/00 |

OTHER PUBLICATIONS

Wong et al.; "Wireless Sensor Seismic Response Monitoring System Implemented on top of NEESgrid"; Health Monitoring and Smart Nondestructive Evaluation of Structural and Biological Systems IV; Proc. of SPIE vol. 5768; pp. 11, 2005.

Alesheikh et al.; "Design and Implementation of Sensor Metadata on Internet"; K.N. Tooshi University, Teheran, Iran; pp. 6, 2002.

Kato et al.; "Home Appliance Control Using Heterogeneous Sensor Networks"; Department of Computer Science, Shizuoka University; pp. 5, 2009.

Jeung et al.; "Effective Metadata Management in Federated Sensor Networks"; Proceeding of the Third IEEE International Conference on Sensor Networks, Ubiquitous, and Trustworthy Computing; pp. 8, 2010.

United States Office Action; U.S. Appl. No. 12/856,780; pp. 48, Sep. 13, 2012.

U.S. Appl. No. 12/856,780; pp. 30, filed Aug. 16, 2010.

Japanese Office Action issued in Patent Appl. No. 2011-177652; 5 pages w/ English translation. Feb. 3, 2015.

* cited by examiner

US 9,107,565 B2

IDENTIFYING AN EVENT OCCURRENCE FROM SENSOR DATA STREAMS

TECHNICAL FIELD

This invention relates generally to the field of sensors and more specifically to identifying an event occurrence from sensor data streams.

BACKGROUND

A user may employ a sensor set to monitor data. The sensor set may comprise one or more sensors that detect information associated with the user. The sensor set may report this information. This information may be stored and/or analyzed to provide useful insights.

SUMMARY OF THE DISCLOSURE

In accordance with the present invention, disadvantages and problems associated with previous techniques for identifying the occurrence of an event from sensor data streams may be reduced or eliminated.

According to one embodiment of the present invention, a method for identifying the occurrence of an event from sensor data streams may be provided. The method may include accessing a plurality of sensor data streams generated by a plurality of sensor sets. Each sensor set may comprise one or more sensors. A sensor data stream may be associated with a user. The user may be co-located with a sensor set that generates the sensor data stream. A relationship between two or more sensor data streams of the plurality of sensor data streams may be identified. The method may further include determining, according to the relationship, that the plurality of sensor data streams corresponds to an event. A notification of an occurrence of the event may be sent.

Certain embodiments of the invention may provide one or more technical advantages. A technical advantage of one embodiment may be that an occurrence of an event may be identified by analyzing a plurality of sensor data streams. Another technical advantage of one embodiment may be that a notification of the occurrence of the event may be sent.

Certain embodiments of the invention may include none, some, or all of the above technical advantages. One or more other technical advantages may be readily apparent to one skilled in the art from the figures, descriptions, and claims included herein.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION OF THE DRAWINGS

Figure 1:
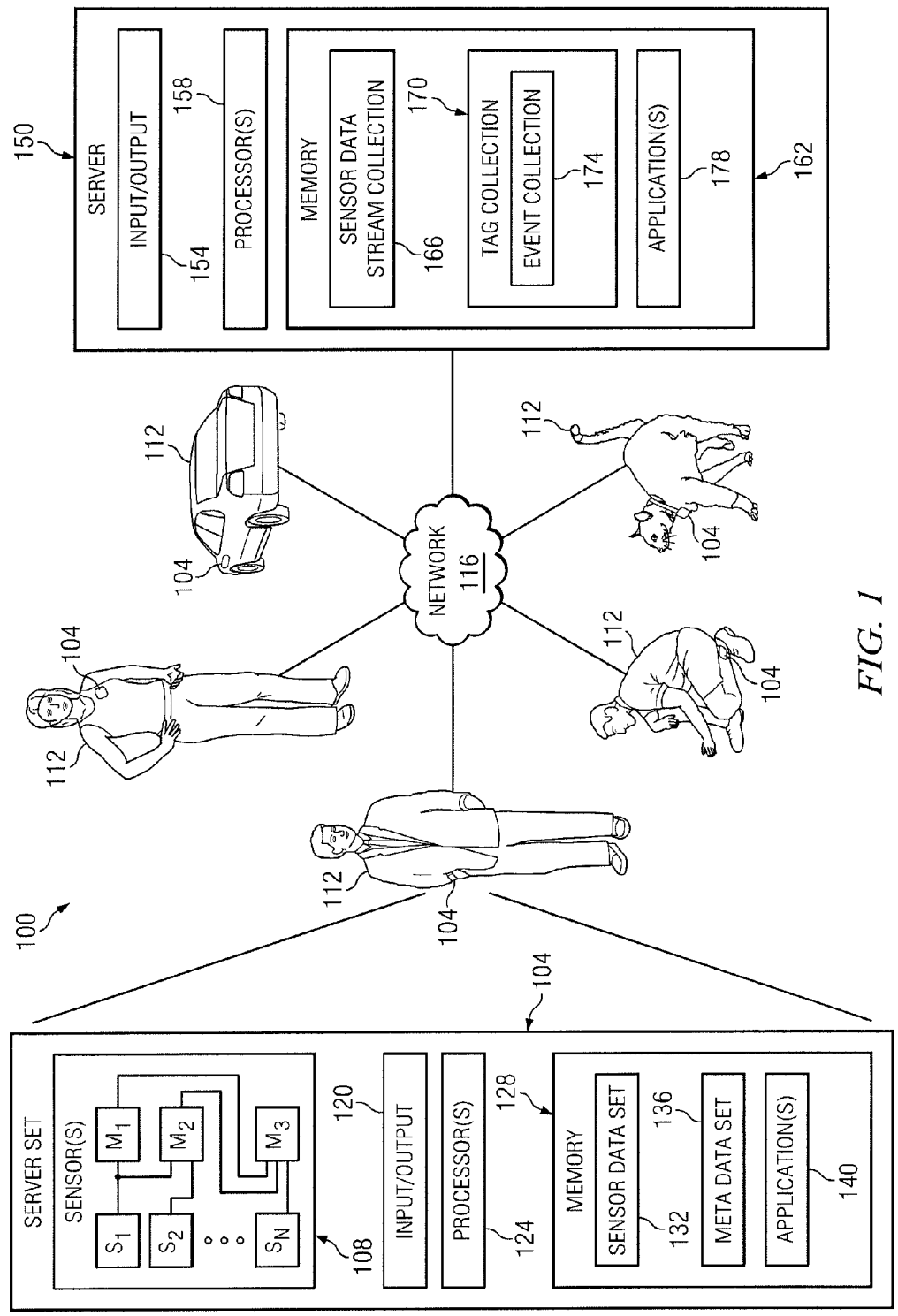
FIG. 1 depicts an example of a system for selecting metadata for sensor data streams.
Figure 2:
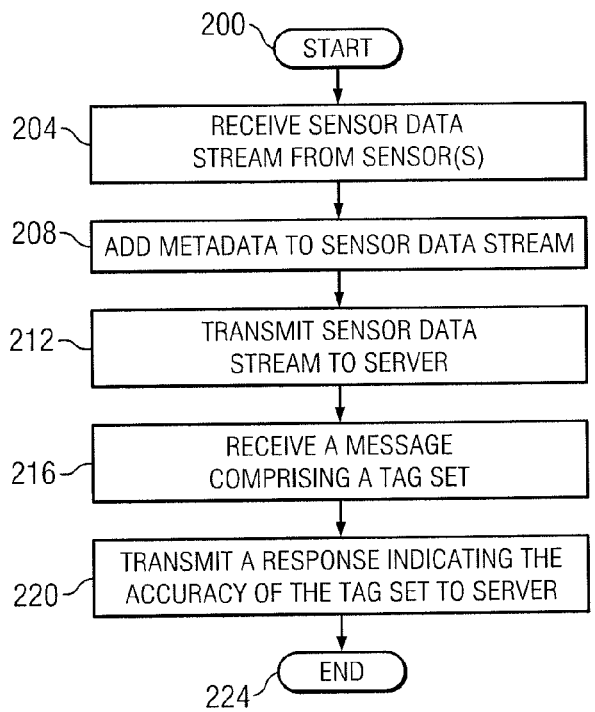
FIG. 2 depicts an example of a method for selecting metadata for sensor data streams that may be performed by a sensor set.
Figure 3:
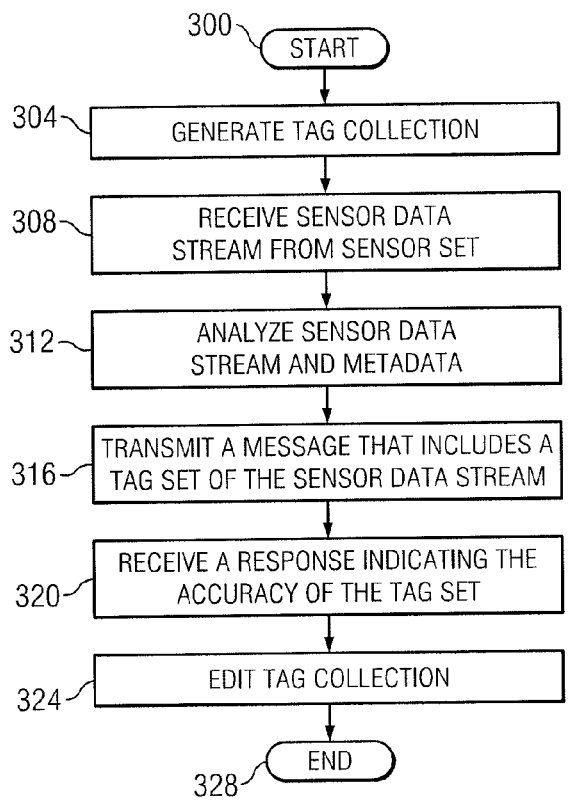
FIG. 3 depicts an example of a method for selecting metadata for sensor data streams that may be performed by a server.

Embodiments of the present invention and its advantages are best understood by referring to FIGS. 1-3 of the drawings, like numerals being used for like and corresponding parts of the various drawings.

FIG. 1 depicts an example of a system 100 for identifying the occurrence of an event from sensor data streams. The system 100 may include users 112, sensor sets 104, network 116, and server 150 coupled as shown. A sensor set 104 may comprise one or more sensors 108. A sensor set 104 may generate one or more sensor data streams. A sensor data stream may be associated with a user 112 co-located with the sensor set 104 that generates the sensor data stream. The system 100 may identify a relationship between two or more sensor data streams. The system 100 may determine, according to the relationship, that the plurality of sensor data streams corresponds to an event. The system 100 may send a notification of an occurrence of the event.

In some embodiments, a user 112 may be any being, object, or set of one or more beings and/or objects, such as a living organism (e.g., a human, animal, or plant) or an inanimate object (e.g., a car or house). A user 112 may be associated with a sensor set 104 and one or more sensors 108 of the sensor set 104. A sensor set 104 and its sensors 108 are associated with a user 112 when the sensors 108 collect information relevant to user 112. For example, as explained below, a sensor 108 may detect location, biometric, environmental, and/or behavioral information of or associated with the user 112. In the embodiment depicted, sensor set 104 also includes memory 128, input and/or output devices 120, and one or more processors 124.

A sensor 108 may be any device capable of detecting and/or processing detected information. In some embodiments, a sensor may detect location information (e.g., latitude, longitude, a location attribute (such as a street address or name of an establishment), elevation), biometric information (e.g., heart rate, body temperature, blood pressure, body movement, breathing rate), environmental information (e.g., temperature, audio, light, weather, smog, pollen), behavioral information (i.e., an action of the user, such as reading, walking, shouting, sleeping, eating, driving, or shaking hands) and/or other information. For example, in some embodiments, a sensor may be a Global Positioning System (GPS) or other location sensor, a thermometer, an actigraph, an accelerometer, a blood pressure sensor, or other suitable measuring device.

In some embodiments, a sensor may be a metasensor (such as $M_1$, $M_2$, or $M_3$) that is operable to process information of one or more other metasensors or sensors $S_1$-$S_N$. In some embodiments, the information processed by a metasensor may be information detected by a sensor (such as $S_1$ or $M_1$), information already processed by a metasensor $M_1$, and/or non-sensor information. In some embodiments, a metasensor $M_1$ may detect a behavior and/or other information of a user 112.

In some embodiments, a sensor 108 may be co-located with a user 112 such that the sensor 108 resides on, within, or near user 112. For example, a sensor 108 may be coupled to or worn by a user 112. In some embodiments, the sensors 108 of a sensor set 104 may be placed in different locations. For example, a first sensor 108 of sensor set 104 may be placed on the wrist of a user 112, and a second sensor 108 of sensor set 104 may be placed on a car driven by the user 112. In some embodiments, a sensor 108 may or may not be co-located with other elements of sensor set 104. For example, a sensor 108 may be removably attached to all or a portion of input and/or output devices 120.

In the embodiment depicted, memory 128 of sensor set 104 comprises sensor data set 132, metadata set 136, and one or more applications 140. Sensor data set 132 may comprise sensor data streams obtained from sensors 108. A sensor data stream may be any form of data used to represent one or more measurements of one or more sensors 108. For example, a sensor data stream may be a plurality of bits that indicate a measurement of 105° Fahrenheit (F) and/or a blood pressure of 120/80 millimeters of mercury (mmHG). In some embodiments, a sensor data stream may represent a series of measurements obtained over a length of time. For example, a sensor data stream may comprise a series of speed measurements obtained at different times. In some embodiments, a sensor data stream may include location, biometric, environmental, behavioral, and/or other information associated with a user 112.

Metadata set 136 may comprise tags that are each associated with one or more sensor data streams of sensor data set 132. A tag may be any type of information that describes a sensor data stream. In some embodiments, a tag may comprise text. For example, "playing tennis," "McDonald's," "traffic jam," or "earthquake" may be tags associated with sensor data streams.

A sensor data stream may be associated with more than one tag. In some embodiments, tags may be grouped into categories such as location, activity, people, or other suitable category. In some embodiments, a sensor data stream may be associated with a tag of each category of a plurality of categories. For example, a sensor data stream may be associated with the tags "McDonald's" (place), "eating" (activity), "Aaron," "Bob," and "Cathy" (people).

In some embodiments, a tag may describe an event. An event may be something that has occurred, is occurring, or will occur. An event may affect a plurality of people. For example, an event may be a fire, riot, incident of severe weather, traffic jam, earthquake, outbreak of disease, proliferation of pollen, or other suitable occurrence.

In some embodiments, a tag may comprise a binary indicator. For example, in some embodiments, a sensor data stream may include a binary indicator of whether the sensor data stream is associated with an occurrence of an event, such as an earthquake or traffic jam. This event indicator may have a default value of "no." In some embodiments, sensor set 104 may include an "event" button that may be pressed in response to an event occurrence. When the event button is pressed, the event indicator value may be set to "yes." In some embodiments, an event indicator may be associated with a sensor data stream that comprises a location measurement to facilitate identification of the location of the event occurrence. In some embodiments, a tag may include binary indicators for particular events (e.g., traffic jam, riot, severe weather, medical emergency), locations (e.g., home, work), activities (e.g., eating, sleeping), or other suitable indicators.

In some embodiments, a tag may include a relative indicator. For example, a user 112 may use a traffic indicator to express the speed of traffic. In some embodiments, a user 112 may select a numeric value (such as a number between 0 and 10) to express the speed of traffic. Such an indicator may be useful if the sensor set 104 associated with a user 112 does not include a sensor 108 capable of measuring traffic speed. As another example, a user 112 may tag a sensor data stream with a value that represents how the user 112 feels. As described later, tags may be correlated with other tags and/or sensor data streams to provide useful information to user 112 and/or other entities. Thus, for example, a user 112 may be able to track his or her wellbeing as it relates to particular tags and/or measurements of sensor data streams.

Tags of metadata set 136 may be created, deleted, edited, selected, assigned, proposed, and/or accepted by any suitable entity, such as all or a portion of sensor set 104 (e.g., a metasensor $M_1$), user 112, a being associated with user 112 (e.g., the owner of a cat to which sensor set 104 is affixed), and/or server 150. In some embodiments, a user 112 may supply a tag that is associated with a sensor data stream.

In some embodiments, a metasensor $M_1$ may supply a tag that is associated with a sensor data stream. In various embodiments, a metasensor may access data output by one or more other sensors (such as $S_1$ and/or $M_1$) and/or non-sensor data, process the accessed data, and output one or more sensor data stream and/or other related information (such as a tag that describes the accessed data). For example, a metasensor may receive one or more sensor data streams, process the sensor data streams, and determine that the sensor data streams correspond to an activity (such as walking, sitting, or riding a bicycle). In some embodiments, the metasensor may output the received sensor data streams and/or a processed form of the received sensor data streams.

A metasensor $M_1$ may process the sensor data streams (and/or other information) and/or select tags in any suitable manner. For example, the metasensor may use any of the methods for selecting tags that are performed by server 150 as described below. In various embodiments, sensor data streams generated by sensors 108 may be transmitted to server 150. Server 150 may access these sensor data streams and select a set of one or more tags for the sensor data streams (e.g., if a tag has not already been supplied by a user 112 (or metasensor $M_1$) or a user 112 desires to associate additional tags with a sensor data stream) and/or analyze sensor data streams with user and/or metasensor defined tags to refine the selection process. In some embodiments, a user 112 (or a being associated with the user) may accept or reject one or more of the selected tags. If a selected tag is accepted, it may be stored in metadata set 136 and associated with one or more of the corresponding sensor data streams of sensor data set 132.

Sensor set 104 may also comprise input and/or output devices 120 that facilitate communication between sensor set 104 and server 150 and/or within sensor set 104. One or more applications 140 may comprise logic that may be executed by one or more processors 124 to facilitate performance of the operations of sensor set 104 described herein.

A sensor set 104 may communicate with a server 150 through network 116. Network 116 may comprise any wireless and/or wired network that enables communication between sensor sets 104 and server 150.

Server 150 may be any computing device operable to receive, process, and/or transmit data. In the embodiment depicted, server 150 comprises input and/or output devices 154, one or more processors 158, and memory 162. The input and/or output devices 154 may facilitate communication between server 150 and a sensor set 104 and/or within server 150. Memory 162 may include sensor data stream collection 166, tag collection 170, and one or more applications 178. The one or more applications 178 may comprise logic that may be executed by the one or more processors 158 to facilitate performance of the operations of the server 150 described herein.

Sensor data stream collection 166 may comprise sensor data streams and metadata (such as tags) associated with the sensor data streams. In some embodiments, at least some of the sensor data streams and/or associated metadata may be received from a sensor set 104. In some embodiments, server 150 may access one or more of the sensor data streams and select tags for the sensor data streams based on other sensor data streams and/or tag collection 170.

Tag collection 170 may comprise tags and criteria for selecting one or more tags for sensor data streams. In some embodiments, tag collection 170 may be accessed by server 150 in order to select a tag for one or more sensor data streams. A tag for a sensor data stream may be selected according to a relationship between the sensor data stream and one or more sensor value range sets associated with the tag. A sensor value range set may comprise one or more sensor value ranges. A sensor value range may specify a range of values for a particular measurement. For example, a sensor value range may be a heart rate of 60-80 beats per minute, a temperature below 32° F., or an elevation above sea level. In some embodiments, a range may be limited to a single value, such as a particular location. In some embodiments, a sensor value range set may specify a series of sensor value ranges. In some embodiments, each sensor value range may correspond to a period of time. For example, a sensor value range set may comprise a first sensor value range for a first period of time, a second sensor value range for a second period of time, and so on.

In some embodiments, a tag may be associated with one or more sensor value ranges. For example, the tag "Yankee Stadium" may be associated with a sensor value range of location measurements that are within 100 meters of the center of Yankee Stadium. As another example, the tag "dance club" may be associated with a first sensor value range that includes volume levels of 95-115 decibels and a second sensor value range that includes rhythmic body motion above a certain amplitude. As another example, the tag "exercising" may be associated with a sensor value range set that has a first sensor value range of 60-80 heart beats per minute at an initial time, a second sensor value range of 90-110 heart beats per minute at a second time, and a third sensor value range of over 120 heart beats per minute at a third time.

In some embodiments, a confidence value of a sensor data stream/tag pair may be assigned according to the relationship between the sensor data stream and the one or more sensor value ranges associated with the tag. A confidence value may represent an indication of the accuracy of the selection of the tag for the sensor data stream. The selection of a tag and/or the calculation of a confidence value may be based on any suitable criteria that defines the relationship between a sensor data stream and one or more sensor value ranges of a tag.

In some embodiments, the selection of a tag and/or calculation of a confidence value may be based on whether the measurements indicated by a sensor data stream are within the sensor value ranges associated with the tag. For example, a sensor data stream that indicates a location 35 meters north of the center of Yankee Stadium and a sensor data stream that indicates a volume level of 100 decibels and a high amplitude of rhythmic body motion may result in the selection of the tags "Yankee Stadium" and "dance club" for the respective sensor data streams. In some embodiments, the confidence values of these sensor data stream/tag pairs may be higher than if the sensor data streams indicated measurements outside of the sensor value ranges. In some embodiments, various confidence levels may be assigned based on where a particular measurement lies within a sensor value range. For example, a higher confidence value may be calculated for a "Yankee Stadium"/sensor data stream pair if the sensor data stream indicates a location 5 meters north of the center of Yankee Stadium as opposed to 99 meters south of the center.

In some embodiments, a tag may be selected and/or a higher confidence value calculated if one or more measurements indicated by a sensor data stream are sufficiently close to the sensor value ranges associated with the tag. For example, the tag "dance club" may be selected for a sensor data stream that indicates high amplitude rhythmic body motion and a volume level of only 90 decibels, even though the volume level is outside of the sensor value range. In some embodiments, such a selection may be conditional upon the measurements of the sensor data stream not being within the sensor value ranges of another tag.

In some embodiments, the selection of the tag and/or calculation of a confidence value may take into account other tags associated with sensor data streams that indicate similar measurements. For example, a series of sensor data streams that indicate a particular location may be associated (e.g., by users 112) with the tag "Dave's party." In such a case, server 150 may select the tag "Dave's party" for a newly received sensor data stream that indicates a similar location and/or calculate a high confidence value for the newly received sensor data stream/"Dave's party" pair.

In some embodiments, a confidence value may be higher for a sensor data stream/tag pair if the tag has been associated with numerous similar sensor data streams. For example, if twenty people tag their respective sensor data streams (that indicate a particular location) with "Dave's party," the confidence value for the newly received sensor data stream/"Dave's party" pair may be higher than if only one person tags a similar sensor data stream.

In some embodiments, the selection of the tag may take into account the time of the creation and/or transmittal of the sensor data stream and/or related sensor data streams. For example, if the newly received sensor data stream of the above example is received a month after the sensor data streams that were previously tagged with "Dave's party," server 150 may elect to not select "Dave's party" and/or may calculate a relatively low confidence value for the sensor data stream/"Dave's party" pair.

In some embodiments, a server 150 may use all or a portion of a sensor data stream when selecting a tag and/or calculating a confidence value. For example, a sensor set 104 may produce a sensor data stream that indicates an ambient temperature, an amplitude of body motion, and a volume level. In some embodiments, the server 150 may or may not use the ambient temperature during selection of one or more tags (such as "dance club") for the sensor data stream and/or a calculation of a confidence value.

In some embodiments, the selection of a tag and/or the calculation of a confidence value may be based on the methods described above, other suitable methods, and/or any combination of methods.

In some embodiments, a tag set of one or more tags may be selected for a sensor data stream. In some embodiments, the tags of a tag set may be selected and/or ranked according to the confidence value of each sensor data stream/tag pair. The tag set may then be reported to any suitable entity, such as user 112, a being associated with user 112, or a system administrator. For example, in some embodiments, one or more tags of the tag set may be proposed for or automatically associated with the corresponding sensor data stream.

In some embodiments, the tag set may be proposed to an entity (such as user 112) that may accept and/or reject one or more tags of the tag set. If a tag is accepted, it may be associated with the corresponding sensor data stream. In some embodiments, if each tag of the tag set is rejected, a second tag set may be selected and proposed by the server 150.

In some embodiments, a tag set of one or more tags may be automatically associated with one or more sensor data streams by the server 150. Server 150 may use any suitable criteria to determine whether to associate a tag with a sensor data stream. For example, in some embodiments, a tag may be automatically associated with the sensor data stream if the confidence value associated with the sensor data stream/tag pair is above a certain threshold and/or is higher (e.g., by a predetermined amount) than the next highest confidence value associated with a different tag.

In the embodiment depicted, tag collection 170 includes event collection 174. Event collection 174 may comprise tags that correspond to events and criteria for determining occurrences of these events. Server 150 may monitor a plurality of sensor data streams of a plurality of different users 112 to identify event related information, such as event occurrences. In some embodiments, a relationship between two or more sensor data streams may indicate an event occurrence.

In some embodiments, an event occurrence may be identified when a predetermined number of sensor data streams comprising information related to an event are received. For example, as explained earlier, a sensor data stream may comprise an event indicator. In some embodiments, if a predetermined number of sensor data streams indicate a particular geographic area and are associated with event indicator values of "yes," then an occurrence of the event may be identified. As another example, in some embodiments, if a predetermined number of sensor data streams have associated tags that describe an event, it may be determined that the event has occurred. For example, if three or more tags of "riot" are received and these tags are associated with sensor data streams that indicate a particular geographic area, an occurrence of a riot may be determined.

In some embodiments, a particular event may be identified according to a relationship between one or more sensor data streams and one or more sensor value ranges associated with a particular event. In some embodiments, if a predetermined number of sensor data streams identify measurements within a sensor value range, an event occurrence may be identified. For example, if three or more sensor data streams (from three different users 112) indicate a particular geographic location and ambient temperatures of over 150° F., an occurrence of a fire may be identified.

In some embodiments, an event occurrence may be identified according to a chronological relationship between sensor data streams. For example, in some embodiments, if the server 150 receives multiple sensor data streams from a common geographic area that indicate sudden heart rate increases followed quickly by acceleration of movement, the server 150 may determine that a riot has occurred. However, in some embodiments, if the acceleration precedes, rather than follows, the heart rate increases, the server 150 may determine that a different event (or no event) has occurred.

In various embodiments, an event may be determined according to a quantity of sensor data streams and confidence levels associated with one or more sensor data stream/event pairs. For example, in some embodiments, an event occurrence may be identified by relatively low confidence values if there are sufficient corroborating sensor data streams. For example, an occurrence of a fire may be indicated by three sensor data streams that indicate temperatures of 140° F., 135° F., and 120° F. respectively. In some embodiments, one sensor data stream may be sufficient to indicate an occurrence of an event if the confidence level of the sensor data stream/event pair is sufficiently high. For example, a sensor data stream that indicates a temperature of 300° F. and a very bright light level may indicate the occurrence of a fire.

In some embodiments, server 150 may receive sensor data streams from various users 112 with heterogeneous sensor sets. That is, a particular user 112 may be associated with a sensor set having one or more sensors 108 that are not included in a sensor set associated with a different user. For example, a particular user 112 may have a certain type and/or brand of sensor that measures an attribute and another user 112 may have a different type and/or brand of sensor that measures the same or a similar attribute. As another example, a particular user 112 may have a sensor that another user does not have. In some embodiments, server 150 may be operable to receive sensor data streams from heterogeneous sensor sets, analyze the sensor data streams, and produce useful information, such as whether an event has occurred and/or other information relating to an event.

In some embodiments, server 150 may use non-sensor information (alone or in combination with the received sensor data streams) to determine that an event has occurred. For example, server 150 may use databases, online lookups, user entered data, or other data to produce event related information.

In some embodiments, the identification of an event occurrence and/or other event related information may be based on the methods described above, other suitable methods, and/or any combination of methods. Event related information may include any information regarding one or more particular events, such as an occurrence of an event, characteristics of an occurrence of an event (such as location, time, or duration of the event), how likely an occurrence of an event is, users 112 associated with an occurrence of an event, or other information.

In some embodiments, an event occurrence may be reported to any suitable entity, such as users 112, beings associated with users 112, the general public, system administrators, police, government officials, and/or emergency response teams. In some embodiments, if the occurrence of an event is known, but the particular event is not, an event notification may be reported and the particular event may be reported after the particular event has been identified. For example, if several users 112 press their respective event buttons, it may be known that an event has occurred, but the exact event may not be identified until additional sensor data streams are received.

In some embodiments, server 150 may be operable to receive queries regarding one or more events. The server 150 may respond with event related information, such as whether the event has occurred.

Using system 100 to identify and report events has many advantages. For example, the system 100 may alert individuals and/or authorities of problem areas and/or situations, such as congested roads, riots, flu epidemics, or other events. In some embodiments, by utilizing information obtained from sensor sets of various users 112, system 100 allows for relatively quick and/or automatic identification and notification of events.

In some embodiments, a tag may be synonymous with one or more other tags. For example, the tags "sick," "ill," and "not feeling well" may each describe the same state of being. In some embodiments, a tag of tag collection 170 may be associated with a list of synonyms. The tag may be considered a "topic tag" and each synonym may be a "synonym tag." In some embodiments, a topic tag may be preferred to a synonym tag during selection of a tag set for a sensor data stream.

In some embodiments, synonym tags may be treated as if they were the corresponding topic tag. For example, if three tags of the topic tag "riot" are required before identifying a riot, two tags of "riot" and one of synonym tag "revolt" may trigger an identification of a riot. As another example, server 150 may modify a sensor value range, confidence level, or other information associated with a topic tag based on a sensor data stream that is tagged with a synonym tag (or vice versa).

In some embodiments, a topic tag may be replaced. For example, if server 150 determines that a synonym tag is more popular than a topic tag, the server 150 may convert the synonym tag to a topic tag and the topic tag to a synonym tag.

In some embodiments, a tag may be related to another tag. In such cases, information associated with one tag may be used to determine the information to be associated with a related tag. For example, sensor data streams tagged with "McDonalds" and "hamburger restaurant" may indicate similar physiological responses of a user 112. Accordingly, a sensor value range and/or a confidence value of the tag "McDonald's" may be used to edit a sensor value range and/or confidence value for the tag "hamburger restaurant."

In some embodiments, related tags may have a "relationship indicator" that specifies how closely related the tags are. In some embodiments, the relationship indicator may be based on the likelihood that the tags have equivalent meanings. In some embodiments, the indicator may be based on how often the tags appear together in one or more collections of text. In some embodiments, the relationship indicator may comprise a numerical weight used to determine a confidence value associated with the tag and/or whether a tag should be selected. For example, if the tags "riot" and "public violence" have a relationship indicator with a weight of 0.6, then a tag of "public violence" may count as 50% of a tag of "riot." Thus, if three tags of "riot" are required before a riot is identified, two tags of "riot" and one tag of "public violence" may not identify a riot, but the reception of an additional tag of "public violence" will.

In some embodiments, tag collection 170 may be edited (e.g., generated and/or updated) in any suitable manner. Any suitable data may be used to edit tag collection 170, such as information originating from a source other than system 100 and/or information obtained by system 100. For example, a database, web page, server 150, sensor set 104, user 112, system administrator, and/or other source may provide information used to edit tag collection 170. In some embodiments, an application 178 may analyze this information and edit tag collection 170 accordingly.

In some embodiments, an application 178 may analyze a collection of text, such as a dictionary, to edit a list of tags. In some embodiments, the application 178 may edit topic tags, synonym tags, and/or relationship indicators of tags. In some embodiments, a database or other source of data may be used to edit sensor value ranges and/or confidence value calculation methodologies.

In some embodiments, server 150 may use metadata transmitted with sensor data streams from sensor set 104 to edit tags. For example, a sensor data stream may be sent with a tag that is not found in collection 170. This tag may be added to tag collection 170 and the sensor data stream may be used to generate the sensor value range associated with the new tag. In some embodiments, sensor value ranges and/or confidence value calculation methodologies may be refined as other sensor data streams with equivalent, synonymous, and/or related tags are received. For example, a user 112 may transmit a sensor data stream that identifies a volume level of 90 decibels and rhythmic body motion of a high amplitude. The user 112 may associate the tag "dance club" with the sensor data stream and transmit the tag and sensor data stream to the server. In response, server 150 may modify the sensor value ranges associated with the tag "dance club" such that sensor data streams that comprise a volume level of 90-115 decibels and adequate body motion are associated with the tag "dance club." In some embodiments, confidence values may be modified in a similar fashion. For example, a confidence value for the "dance club" tag and a sensor data stream with a volume level of 90 decibels may be increased.

In some embodiments, a response received by a server 150 may to used to edit tag collection 170. As described above, server 150 may transmit a tag set to an entity, such as a user 112, and the entity may respond by accepting or rejecting the tags of the tag set. In some embodiments, server 150 may use this response to edit tag collection 170. For example, server 150 may use the response to modify a sensor value range associated with a tag. As another example, server 150 may modify a confidence level calculation methodology associated with a tag.

In some embodiments, server 150 may be operable to calculate correlations between sensor data streams and/or tags. In some embodiments, server 150 may calculate the probability of a particular measurement of a sensor data stream or tag based on the existence of another sensor data stream or tag. For example, server 150 may use stored sensor data stream collection 166 and/or tag collection 170 to calculate that user 112 has an 80% chance of drinking alcohol if the user 112 attends a dance club. These calculations may be specific to the user or calculated based on a group of users 112, such as all users 112.

In some embodiments, server 150 may calculate biometric statistics for a user 112. For example, users 112 may be able to monitor their blood pressure, heart rate, breathing rate, and/or other physical indicator before, during, and/or after a particular activity.

In some embodiments, server 150 may calculate an expected value of a measurement of a sensor data stream based on previous measurements of sensor data streams. For example, server 150 may calculate an average speed on a particular stretch of freeway for a future time based on previous speeds identified by sensor data streams.

FIG. 2 depicts an example of a method for selecting metadata for sensor data streams that may be performed by a sensor set 104. The method begins at step 200. At step 204, sensor set 104 receives a sensor data stream from one or more sensors 208. The sensor data stream may be stored in sensor data set 132. The sensor data stream may indicate one or more measurements of the one or more sensors 208.

At step 208, user 112 adds metadata to the sensor data stream. For example, user 112 may enter a tag that describes the sensor data stream. As another example, the sensor data stream may be processed and/or tagged by one or more metasensors $M_1$-$M_3$. The tag may be associated with the sensor data stream and stored in metadata set 136. At step 212, the sensor data stream is transmitted by the sensor set 104 across network 116 to server 150. The sensor data stream may be transmitted by any suitable means. The sensor data stream may be transmitted with its associated metadata.

At step 216, the sensor data stream receives a message comprising a tag set from server 150. In some embodiments, the tag set may comprise one or more tags that may describe the sensor data stream. In some embodiments, the tag set may be automatically assigned to the previously transmitted sensor data stream. In various embodiments, the user 112 may view the tag set and accept and/or reject one or more tags. In some embodiments, the tag set may comprise one or more tags that indicate an event occurrence.

At step 220, the sensor set 104 transmits a response to server 150 that indicates the accuracy of the tag set. For example, the response may indicate which tags were accepted or rejected by user 112. The method ends at step 224.

Modifications, additions, or omissions may be made to the method of FIG. 2 without departing from the scope of the invention. The method may include more, fewer, or other steps. For example, in some embodiments, the user 112 may omit step 208, that is, the user 112 may leave a sensor data stream unassociated with a tag. As another example, in some embodiments, step 216 may be omitted if the user 112 has already associated a tag with the sensor data stream and does not desire to associate additional tags with the sensor data stream. Additionally, steps may be performed in any suitable order.

FIG. 3 depicts an example of a method for selecting metadata for sensor data streams that may be performed by a server 150. The method begins at step 300. At step 304, a tag collection 170 of server 150 is generated. In some embodiments, tags of tag collection 170 may be generated by analyzing one or more collections of text. In some embodiments, tag selection criteria is generated and associated with the tags of tag collection 170.

At step 308, a sensor data stream is received from a sensor set 104. The sensor data stream may or may not have one or more tags associated with it. At step 312, server 150 analyzes sensor data streams and any accompanying metadata. In some embodiments, server 150 may select a tag set of one or more tags to describe the sensor data streams. For example, one or more tags may be selected according to a relationship between the sensor data stream and one or more sensor value ranges associated with the tags. In some embodiments, server 150 may identify an event occurrence based on an analysis of the sensor data streams and/or metadata.

At step 316, server 150 transmits a message that includes the tag set of the sensor data stream. The tag set may include one or more tags that describes the sensor data stream received at step 308. In some embodiments, the tag set may indicate an event occurrence.

At step 320, the server 150 receives a response that indicates the accuracy of the tag set. For example, the response may indicate an acceptance or rejection of one or more tags of the tag set. As another example, a response may indicate confirmation of the event occurrence.

At step 324, the server 150 edits tag collection 170. In some embodiments, the server 150 may edit the tag collection based on a sensor data stream and accompanying metadata, a response indicating the accuracy of a message, and/or other sources. The method ends at step 328.

Modifications, additions, or omissions may be made to the method of FIG. 3 without departing from the scope of the invention. The method may include more, fewer, or other steps. Additionally, steps may be performed in any suitable order.

Modifications, additions, or omissions may be made to the systems and apparatuses disclosed herein without departing from the scope of the invention. The components of the systems and apparatuses may be integrated or separated. For example, all or a portion of sensor set 104 may be integrated with server 150.

Moreover, the operations of the systems and apparatuses may be performed by more, fewer, or other components. For example, the operations of sensor set 104 and server 150 may be performed by one component, or the operations of server 150 may be performed by more than one component. Additionally, operations of the systems and apparatuses may be performed using any suitable logic comprising software, hardware, and/or other logic. As used in this document, "each" refers to each member of a set or each member of a subset of a set.

A component of the systems and apparatuses disclosed herein may include an interface, logic, memory, and/or other suitable element. An interface receives input, sends output, processes the input and/or output, and/or performs other suitable operation. An interface may comprise hardware and/or software.

Logic performs the operations of the component, for example, executes instructions to generate output from input. Logic may include hardware, software, and/or other logic. Logic may be encoded in one or more tangible media and may perform operations when executed by a computer. Certain logic, such as a processor, may manage the operation of a component. Examples of a processor include one or more computers, one or more microprocessors, one or more applications, and/or other logic.

In particular embodiments, the operations of the embodiments may be performed by one or more computer readable media encoded with a computer program, software, computer executable instructions, and/or instructions capable of being executed by a computer. In particular embodiments, the operations of the embodiments may be performed by one or more computer readable media storing, embodied with, and/or encoded with a computer program and/or having a stored and/or an encoded computer program.

A memory stores information. A memory may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable medium.

Although this disclosure has been described in terms of certain embodiments, alterations and permutations of the embodiments will be apparent to those skilled in the art. Accordingly, the above description of the embodiments does not constrain this disclosure. Other changes, substitutions, and alterations are possible without departing from the spirit and scope of this disclosure, as defined by the following claims.

What is claimed is:

1. A method comprising:
receiving a plurality of sensor data streams generated by a plurality of sensor sets, each sensor set comprising one or more sensors, a sensor data stream associated with a user co-located with a sensor set that generates the sensor data stream, the sensor data stream comprising measurements of the sensor;
identifying a relationship between the measurements included in two or more sensor data streams of the plurality of sensor data streams;
determining one or more confidence values associated with the measurements included in the two or more sensor data streams;
determining, according to the relationship and to the one or more confidence values, that the plurality of sensor data streams correspond to an occurrence of an event that was measured by the plurality of sensor sets and represented in the measurements included in the two or more data streams, the determining that the plurality of sensor data streams correspond to the occurrence of the event comprising:
accessing a collection of events, each event associated with two or more sensor value ranges; and
identifying the event from the collection of events according to a second relationship between two or more sensor data streams of the plurality of sensor data streams and the two or more sensor value ranges associated with the event; and
sending a notification of the occurrence of the event.

2. The method of claim 1, the determining, according to the relationship, that the plurality of sensor data streams correspond to an occurrence of an event further comprising:
accessing metadata that describes a sensor data stream of the plurality of sensor data streams; and
identifying the event according to the metadata.

3. The method of claim 1, further comprising:
accessing metadata that describes a sensor data stream of the plurality of sensor data streams; and
updating a collection of events according to the metadata and the sensor data stream.

4. The method of claim 1, further comprising:
receiving a response indicating whether the event accurately describes one or more sensor data streams of the plurality of sensor data streams; and
updating a collection of events according to the response.

5. The method of claim 1, the plurality of sensor data streams communicating a location of a user.

6. The method of claim 1, the plurality of sensor data streams communicating biometric data of a user.

7. The method of claim 1, the plurality of sensor data streams communicating environmental data associated with a user.

8. The method of claim 1, the plurality of sensor data streams communicating a behavior of a user.

9. One or more tangible non-transitory computer-readable media having computer-executable code, when executed by a computer operable to:
receive a plurality of sensor data streams generated by a plurality of sensor sets, each sensor set comprising one or more sensors, a sensor data stream associated with a user co-located with a sensor set that generates the sensor data stream, the sensor data stream comprising measurements of the sensor;
identify a relationship between the measurements included in two or more sensor data streams of the plurality of sensor data streams;
determine one or more confidence values associated with the measurements included in the two or more sensor data streams;
determine, according to the relationship and to the one or more confidence values, that the plurality of sensor data streams correspond to an occurrence of an event that was measured by the plurality of sensor sets and represented in the measurements included in the two or more data streams, the determining that the plurality of sensor data streams correspond to the occurrence of the event comprising:
accessing a collection of events, each event associated with two or more sensor value ranges; and
identifying the event from the collection of events according to a second relationship between two or more sensor data streams of the plurality of sensor data streams and the two or more sensor value ranges associated with the event; and
send a notification of the occurrence of the event.

10. The media of claim 9, the determining, according to the relationship, that the plurality of sensor data streams correspond to an occurrence of an event further comprising:
accessing metadata that describes a sensor data stream of the plurality of sensor data streams; and
identifying the event according to the metadata.

11. The media of claim 9, when executed by a computer further operable to:
access metadata that describes a sensor data stream of the plurality of sensor data streams; and
update a collection of events according to the metadata and the sensor data stream.

12. The media of claim 9, when executed by a computer further operable to:
receive a response indicating whether the event accurately describes one or more sensor data streams of the plurality of sensor data streams; and
update a collection of events according to the response.

13. The media of claim 9, the plurality of sensor data streams communicating at least one of:
a location of a user;
biometric data of a user;
environmental data associated with a user; and
a behavior of a user.

14. A system comprising:
one or more processors;
a memory that stores logic operable to:
receive a plurality of sensor data streams generated by a plurality of sensor sets, each sensor set comprising one or more sensors, a sensor data stream associated with a user co-located with a sensor set that generates the sensor data stream, the sensor data stream comprising measurements of the sensor;
identify a relationship between the measurements included in two or more sensor data streams of the plurality of sensor data streams;
determine one or more confidence values associated with the measurements included in the two or more sensor data streams;
determine, according to the relationship and to the one or more confidence values, that the plurality of sensor data streams correspond to an occurrence of an event that was measured by the plurality of sensor sets and represented in the measurements included in the two or more data streams, the determining that the plurality of sensor data streams correspond to the occurrence of the event comprising:
accessing a collection of events, each event associated with two or more sensor value ranges; and
identifying the event from the collection of events according to a second relationship between two or more sensor data streams of the plurality of sensor data streams and the two or more sensor value ranges associated with the event; and
send a notification of the occurrence of the event.

15. The system of claim 14, the determining, according to the relationship, that the plurality of sensor data streams correspond to an occurrence of an event further comprising:
accessing metadata that describes a sensor data stream of the plurality of sensor data streams; and
identifying the event according to the metadata.

16. The system of claim 14, the logic further operable to:
access metadata that describes a sensor data stream of the plurality of sensor data streams; and
update a collection of events according to the metadata and the sensor data stream.

17. The system of claim 14, the logic further operable to:
receive a response indicating whether the event accurately describes one or more sensor data streams of the plurality of sensor data streams; and
update a collection of events according to the response.

18. The system of claim 14, the plurality of sensor data streams communicating at least one of:
a location of a user;
biometric data of a user;
environmental data associated with a user; and
a behavior of a user.

* * * * *